United States Patent [19]

Hoff et al.

[11] Patent Number: 4,864,070

[45] Date of Patent: Sep. 5, 1989

[54] PROCESS FOR THE SEPARATION OF ORTHO CHLORINATED AROMATIC ISOMERS BY SELECTIVE ADSORPTION

[75] Inventors: Melvern C. Hoff, Warrenville; Raymond C. Feld, Winfield, both of Ill.

[73] Assignee: Amoco Corporation, Chicago, Ill.

[21] Appl. No.: 172,776

[22] Filed: Mar. 28, 1988

[51] Int. Cl.$^4$ ............................................. C07C 7/12
[52] U.S. Cl. ................................. 585/828; 585/820; 208/310 Z
[58] Field of Search .................... 208/310 R, 310 Z; 585/820, 828

[56] References Cited

U.S. PATENT DOCUMENTS 4,482,776 11/1984 Rosenfeld et al. ............. 208/310 R

*Primary Examiner*—Glenn Caldarola
*Attorney, Agent, or Firm*—Gunar J. Blumberg; William H. Magidson; Ralph C. Medhurst

[57] ABSTRACT

A process is disclosed for separation of ortho chlorotoluene and ortho-dichlorobenzene from their meta and para isomers by use of a specific crystalline aluminophosphate adsorbent which selectively removes the above ortho aromatic isomers. The selectively adsorbed ortho aromatic isomers are removed from the adsorbent through a desorption step.

6 Claims, No Drawings

PROCESS FOR THE SEPARATION OF ORTHO CHLORINATED AROMATIC ISOMERS BY SELECTIVE ADSORPTION

BACKGROUND OF THE INVENTION

The field of art to which the claimed invention pertains is chlorinated aromatic hydrocarbon separation. More specifically, the claimed invention relates to the separation of ortho chlorotoluene and ortho-dichlorobenzene from their meta and para isomers by use of a specific crystalline aluminophosphate adsorbent which selectively removes the above ortho aromatic isomers. The selectively adsorbed ortho aromatic isomers are removed from the adsorbent through a desorption step.

DESCRIPTION OF THE PRIOR ART

It is known in the separation art that certain adsorbents generally comprising crystalline aluminosilicates can be utilized to separate certain hydrocarbons from mixtures thereof. In aromatic hydrocarbon separation and in particular the separation of $C_8$ aromatic isomers, it is generally recognized that certain crystalline aluminosilicates containing selected cations at the zeolitic cationic sites enhances selectivity of the zeolite for a given $C_8$ aromatic isomer. This manner of separation is particularly useful when the components to be separated have similar physical properties, such as freezing and boiling points.

A number of processes describing the separation of para-xylene from a mixture of at least one other xylene isomer utilizing a crystalline aluminosilicate adsorbent are shown in U.S. Pat Nos. 3,558,730, 3,558,732, 3,626,020, and 3,663,638. Other processes which describe the adsorption separation of ethylbenzene from a mixture of xylene isomers utilizing a crystalline aluminosilicate adsorbent are shown in U.S. Pat Nos. 3,943,182, 3,997,619, 3,998,901, 4,021,499 and 4,482,776. U.S. Pat. No. 4,376,226 describes a method of separating ortho-xylene from an aromatic hydrocarbon feed stream by use of a crystalline aluminosilicate adsorbent CSZ-1. U.S. Pat. No. 4,482,776 discloses a method for separating ortho aromatic isomers from a mixture by contacting the feed stream with a bed of the crystalline aluminophosphate adsorbent $AlPO_4$-5. While the separation of dihalobenzene mixtures by adsorption using Na-type zeolites, and Ag-K-Y and Ag-Na-Y zeolites, is known in the art, Japanese KOKAI No. 58/150524 and Japanese KOKAI No. 58/131924, the separation of ortho-chlorotoluene or ortho-dichlorobenzene from a feed stream mixture containing meta and para isomers of these compounds using a crystalline aluminophosphate adsorbent $AlPO_4$-5 is not known in the art.

Ortho-chlorotoluene is used commercially in manufacture of pesticides, dyestuffs, pharmaceuticals and as a solvent. Ortho-dichlorobenzene is used as a solvent in manufacture of toluene diisocyanates, as a cleaning compound and to make 3,4-dichloroaniline, an intermediate for dyes and agricultural chemicals. However, availability of these ortho aromatic isomers is restricted due to the inability to effectively separate these ortho aromatic isomers from their meta and para isomers.

SUMMARY OF THE INVENTION

The invention comprises an adsorptive separation process for the separation of ortho-chlorotoluene or ortho-dichlorobenzene from mixtures of meta and para isomers of these compounds by contacting the chlorinated aromatic hydrocarbon feed stream with a bed of the crystalline aluminophosphate adsorbent $AlPO_4$-5 molecular sieve. A raffinate stream is then withdrawn from the bed, this stream containing less of the selectively adsorbed ortho isomer. The adsorbed ortho isomer on the bed is then desorbed to effect displacement of the ortho isomer, followed by withdrawing from the adsorbent bed an extract stream containing the ortho aromatic isomer. The $AlPO_4$-5 adsorbent is cation exchanged to increase the ortho aromatic selectivity of the adsorbent.

DETAILED DESCRIPTION OF THE INVENTION

A chlorinated aromatic hydrocarbon feed stream which can be utilized in the process of this invention contains mixtures of ortho-, meta-, and para-chlorotoluene or ortho-, meta- and para-dichlorobenzene.

The chlorinated aromatic hydrocarbon feed stream is then contacted with a bed of crystalline aluminophosphate adsorbents, entitled $AlPO_4$-5, having an essential crystalline framework structure whose chemical composition expressed in terms of molar ratios of oxides is $Al_2O_3:1.0\pm0.2\ P_2O_5$, the said framework structure being microporous in which the pores are uniform and in each species having nominal diameters within the range of from 3 to 10 Angstroms and an intracrystalline adsorption capacity for water at 4.6 torr and 24° C. of at least 3.5 weight percent, the adsorption of water being completely reversible while retaining the same essential framework topology in both the hydrated and dehydrated state. By the term "essential framework topology" is meant the spatial arrangement of the primary Al-O and P-O bond linkages. No change in the framework topology indicates that there is no disruption of these primary bond linkages.

The present aluminophosphates are prepared by the method described in U.S. Pat. No. 4,310,440, incorporated herein by reference.

The $AlPO_4$-5 adsorbent can be combined with a binder, such as natural or synthetic clays (e.g. Koalin), inorganic oxides, and lubricants (e.g. graphite) and can be in any form acceptable to the separation process such as extrudates, spheres, granules or tablets.

Certain characteristics of adsorbents are highly desirable, if not absolutely necessary, to the successful operation of a selective adsorption process. Among such characteristics are: adsorptive capacity for some weight of the ortho aromatic isomer per weight of adsorbent; and the selective adsorption of the ortho aromatic isomer with respect to a raffinate component and the desorbent material.

The process for separating ortho-chlorotoluene toluene or ortho-dichlorobenzene from mixtures with their corresponding meta and para isomers comprises (a) contacting the mixture of isomers with crystalline aluminum phosphate molecular sieve adsorbent, (b) removing from said adsorbent a raffinate stream containing less of the ortho isomer than contained in the feed, (c) displacing the adsorbed mixture, rich in the ortho isomer, with a suitable desorbent, and (d) separating the ortho rich adsorbate from the desorbent, for example by distillation. The process can be carried either in a batch system or a continuous flow system at ambient temperature.

Examples of the mixtures which can be separated are ortho-chlorotoluene from its meta and para isomers, and ortho-dichlorobenzene from its meta and para isomers. These are all close boiling mixtures which are costly to separate by fractionation. Crystallization can sometimes be used to separate the para isomer so the disclosed process provides a complementary process for obtaining the ortho isomer. Use of either process would provide an improved feedstock for the other.

Choice of the desorbent is a critical part of the process. Generally a material which has an affinity for the adsorbent between that of the ortho isomer and that of the remaining isomers is preferred. A second requirement is that the desorbent distills at a sufficiently different temperature so as to provide easy separation of raffinate and eluent from the desorbent. It is sometimes desirable for the desorbent to be higher boiling than the raffinate and the product. For optimum performance desorbent materials should have a separation factor equal to about 1 or less than 1 with respect to all extract components so that all of the extract components can be extracted as a class and all raffinate components clearly rejected into the raffinate stream. Suitable desorbents are toluene, benzene, chlorotoluene, dichlorobenzene, ethyltoluene, and chlorobenzene. Preferred desorbents are toluene and chlorobenzene. Toluene is more preferred.

Separation factors can be expressed in terms of the ratio of the two components of the adsorbed phase over the ratio of the same two components in this unadsorbed phase at equilibrium conditions. Separation factor $\beta$ can be expressed in the following equation:

$$\text{Separation Factor } \beta = \frac{(\text{Wt \% Component } A \text{ in adsorbent})/(\text{Wt \% Component } A \text{ in liquid})}{(\text{Wt \% Component } B \text{ in adsorbent})/(\text{Wt \% Component } B \text{ in liquid})}$$

Where separation factor $\beta$ of two components approaches 1.0 there is no preferential adsorption of one component by the adsorbent with respect to the other; they are both adsorbed (or nonadsorbed) to about the same degree with respect to each other. As the separation factor becomes less than or greater than 1.0 there is preferential adsorption by the adsorbent for one component with respect to the other. When comparing the separation factor by the adsorbent of one component A over component B, a separation factor larger than 1.0 indicates preferential adsorption of component A within the adsorbent. A separation factor less than 1.0 would indicate that component B is preferentially adsorbed leaving an unadsorbed phase richer in component A and an adsorbed phase richer in component B. In the separation of ortho aromatic isomers, a separation factor of at least 1.5 to 2.0 of the ortho aromatic isomer over at least one of the other components of the feed stream is preferable.

It has been found that AlPO$_4$-5 molecular sieve selectively adsorbs ortho-substituted benzene isomers from mixtures with meta and para isomers. This separation cannot be based primarily on molecular size and shape because large separation factors are obtained between compounds of similar molecular dimension.

Such selectivity is not common and is reported for only two other sieves, cesium- and/or thallium-modified aluminosilicate disclosed in U.S. Pat. No. 4,309,313, and disclosed for separation of ortho-xylene in U.S. Pat. No. 4,376,226, and a sieve disclosed by D. B. Broughton, Chem. Eng. Prog., October, 1977, p 49.

Results from the measurement of separation factors for 25 compounds relative to ortho-xylene indicate that the basis for the selectivity is mostly electronic and based on charge distribution. Thus, as electron withdrawing groups such as —Cl and —F are added to the ring, or replace —CH$_3$ groups, affinity for the AlPO$_4$-5 increases. With the exception of benzene→toluene→ortho-xylene, adding a —CH$_3$ group decreases this affinity. Replacement of —CH$_3$ by —C$_2$H$_5$ also decreases this affinity, but for reasons which are not apparent.

To determine other separation capabilities of the AlPO$_4$-5 sieve, a series of batch, vial tests, were run to determine relative separation factors between ortho-xylene and a series of alkyl- and halo-substituted and poly-substituted benzenes.

Ortho-xylene was included as one of the components of the test mixtures so that separation factors relative to a common reference, i.e., ortho-xylene, could be calculated directly.

As is the case with other sieves, steric requirements cannot be a critical factor affecting selectivity. The pore diameter in AlPO$_4$-5 is 8 Å, (ACS Symposium, 218 (1983) p 102)). As shown in Table I below, the minimum molecular widths for most of the compounds tested are all less than 8 Å and many show only very small differences in width despite large differences in relative separation factor. For example, ortho-xylene and meta-xylene show the same minimum molecular width and differ by a factor of 10 in relative separation factor.

TABLE I

Minimum Molecular Width of Substituted Benzenes and Separation Factors Relative to O—Xylene

| Compound | Minimum Width, Å(a) | Separation Factor Relative to Ortho Xylene |
|---|---|---|
| Benzene | 6.8 | 0.35 |
| Toluene | 6.8 | 0.550 |
| para-Xylene | 6.8 | 0.113 |
| o-Difluorobenzene | 7.2 | 6.39 |
| ortho-Xylene | 7.6 | 1.0 |
| meta-Xylene | 7.6 | 0.069 |
| Hexafluorobenzene | 7.6 | 12.1 |
| o-Chlorotoluene | 7.6 | 1.633 |
| m-Chlorotoluene | 7.6 | 0.179 |
| 1,2,4-Trimethylbenzene | 7.6 | 0.009 |
| Durene | 7.6 | 0.26 |
| o-Bromotoluene | 7.8 | 0.49 |
| p-Chlorotoluene | | 0.076 |
| o-Dichlorobenzene | | 1.948 |
| p-Dichlorobenzene | | 0.291 |
| m-Dichlorobenzene | | 0.258 |

(a) Determined from covalent bond radii and Van der Waals radii of atoms, The Nature of the Chemical Bond, L. Pauling, Cornell University Press, Ithaca, N.Y., p. 160 (1972).

Several trends are apparent in Table I. Starting with xylenes, toluene, or benzene and either adding chlorine or replacing a methyl group with chlorine, and in turn replacing these with fluorine or adding more fluorine successively increases the affinity of the adsorbate for the AlPO$_4$-5. Adding alkyl groups, with the exception of benzene to toluene, decreases affinity. These effects can be explained on the basis of either withdrawing or contributing electrons to the pi cloud of the ring. The differences between ortho, para, and meta isomers are large and consistent, but are not consistent with relative basicities. No explanation is offered for the large decrease in affinity resulting from replacing a methyl group with an ethyl group and the reverse effect in replacing an ethyl group with a propyl group.

Separation factors are tabulated in Table II relative to ortho-xylene. The ($\beta$) separation factor indicates the relative separation of the ortho isomer from the para isomer, i.e., the ortho isomer is adsorbed preferentially over the adsorption of the para isomer by the adsorbent AlPO$_4$-5

TABLE II

| Compound | Isomers | | | Ethyl-benzene | ($\beta$) ortho/para |
|---|---|---|---|---|---|
| | Ortho | meta | para | | |
| C$_8$ Aromatics | 1 | .068 | 0.115 | .09 | 8.7 |
| Chlorotoluene | 1.35 | 0.179 | 0.25 | — | 5.4 |
| Dichlorobenzene | 1.75 | 0.258 | 0.86 | — | 2.03 |
| Ethyltoluene | 0.06 | .01 | 0.032 | — | 1.87 |

Generally a separation factor ($\beta$) of about 2 is regarded as sufficient to provide adequate separation for a process and this criterion is met in the above examples. The above runs indicate that chlorotoluene as well as dichlorobenzene can be used as a desorbent. Ethyltoluene may also be used, although ethyltoluene is not as efficient as chlorotoluene or dichlorobenzene.

In the experimental procedures, a Hewlett-Packard 5880, Level 4 gas chromatograph fitted with capillary columns and an auto-sampler was employed for all sample analyses.

The column used was a 60-meter OV-351 fused-silica, glass capillary column manufactured by J&W Scientific Corporation, 91 Blue Ravine Road, Folsom, Calif. The OV-351 column has several advantages over a Carbowax 20M glass capillary column, manufactured by Supelco, Inc. Bellefonte, Pa., which can be used. It is very flexible and easily installed, and column stability is a definite advantage. The OV-351 column, after a year's service, had no significant loss of resolution even though thousands of samples had passed through it.

Cyclododecane was used as internal standard for all analyses.

Previous work had indicated that adsorbed water may interfere with adsorption properties of sieves. Therefore, the AlPO$_4$-5 was dried at 165° C. then heated at 94° C./hr. in a forced draft oven to 538° C. The temperature was held constant for 8 hours, then lowered to 165° C. This calcination procedure was performed on all samples overnight prior to experimental use. Immediately prior to experimental use, the sample was cooled to room temperature in a N$_2$ atmosphere dry box. Care was taken not to expose the adsorbent to water during all steps of experimentation.

Two methods of testing AlPO$_4$-5 for separations were used; batch vial experiments to measure separation factors for all the compounds tested, and various flow systems to study kinetic effects.

In a typical batch vial example, one gram of AlPO$_4$-5 and ~3.5 grams of feed of known composition were sealed in a 15 ml glass centrifuge tube fitted with a 12/18 ground glass joint and matching teflon stopper. Care was taken so that no sieve or feed was trapped in the joint allowing leakage and loss of accuracy. Also, all weighings of feed and adsorbent were on a four-place analytical balance to minimize error in this extremely sensitive experimental procedure.

The slurry was allowed to come to equilibrium overnight (16 hours) in an oscillating shaker. Each tube was then centrifuged in a Clay-Adams four-place clinical centrifuge for approximately five minutes and the supernatant liquid removed and analyzed by gas chromatography. From the differences in composition of the supernatant liquid compared to the feeds, the capacity and selectivity of the adsorbent was calculated.

The experimental flow system consisted of two Constametric L.C. pumps, manufactured by Laboratory Data Control, Riviera Beach, Fla., connected to an L.C. column packed with an adsorbent. One pump was used for feed and the other for the desorbent. The L.C. columns used were manufactured by Bethesda Research Labs, Gaithersburg, Md. Several sizes of columns, ranging in size from 30 cm×0.90 cm ID to 120 cm×0.90 cm ID were used. AlPO$_4$-5 was packed into columns after soaking for approximately 1 hour in toluene to force all gases out so the adsorbent bed contained no bubbles during runs. However, even with soaking, some bubbles were observed during runs, probably from dissolved gases in the liquids coming out of solution. The slurry was then poured into a Fischer-Porter bottle and pumped into the top of the column with a continuous liquid flow. A vibrator was used to settle the adsorbent bed while the slurry was being pumped in. This method of packing the adsorbent bed reduced channelling encountered when dry packing an adsorbent bed and resulted in a very consistent adsorbent bed. During a run, effluent samples were taken continuously and weighed and analyzed.

In summary, the instant invention comprises an adsorptive separation process for separating an ortho aromatic compound selected from the group consisting of ortho-chlorotoluene and ortho-dichlorobenzene from a chlorinated aromatic hydrocarbon feed stream comprising a mixture of meta and para isomers of said ortho aromatic compound which comprises contacting said chlorinated aromatic hydrocarbon feed stream with a bed of a crystalline aluminophosphate adsorbent of AlPO$_4$-5; withdrawing from said bed of adsorbent a raffinate stream containing less of the selectively adsorbed ortho aromatic compound of the feed stream; desorbing the adsorbed ortho aromatic compound with a desorbent to effect displacement thereof; and withdrawing from the adsorbent bed an extract stream containing the ortho aromatic compound. In more detail, the said chlorinated aromatic hydrocarbon feed stream comprises the said ortho aromatic compound and a mixture of aromatic hydrocarbons, that is, the said feed stream can comprise the said ortho aromatic compound and a mixture of benzene and chlorinated aromatic hydrocarbons. Also, the said feed stream can comprise the said ortho aromatic compound and a mixture of toluene and chlorinated aromatic hydrocarbons.

The said desorbent is selected from the group consisting of toluene, benzene, chlorotoluene, dichlorobenzene, ethyltoluene, and chlorobenzene. The said desorbent is probably tolune.

The following examples are presented to facilitate the understanding of the present invention. It is to be understood that these examples are presented for the purpose of illustration only and are not intended to limit the scope of the invention.

Although the invented process can be operated without prior purification of the feed stream, the invented process is preferably operated with prior purifiction of the feed stream to concentrate the desired products of the invented process.

Examples I to IV are presented to exemplify the recovery of ortho-xylene from a C$_8$ feed using toluene as a desorbent. Examples V and VI are presented to exemplify the recovery of ortho-chlorotoluene and ortho-dichlorobenzene from C$_8$ feed streams, the data being relative to recovery of ortho-xylene using toluene as a desorbent.

EXAMPLE I

A 30 cm×0.9 cm column was packed with 18.35 grams of $AlPO_4$-5 (9044-96, 83% crystalline) in a toluene slurry. The $AlPO_4$-5 was <75 microns. A mixture containing 25% of each of ortho-, meta-, para-xylene and ethylbenzene was then pumped through the column at a rate of 0.625 g/min. at room temperature. After 25 grams of effluent were removed, the $C_8$ aromatic feed was replaced with toluene at a flow rate of 0.678 g/min and operation continued until substantially all of the $C_8$ aromatics had eluted. Weight balances are summarized in Table III as Run 8528-1.

EXAMPLE II

Using the same packed column as in the previous run, an equimolar mixture of ortho-, meta-, para-xylene and ethylbenzene was pumped into the column at room temperature but at a rate of 0.304 g/min. After 25.3 grams of effluent were obtained and the composition had returned to essentially that of the feed, the mixed $C_8$ aromatics were replaced with toluene at a rate of 0.303 g/min. until a total of 64.7 grams of aromatics had passed through the column and substantially all of the $C_8$ aromatics had eluted. Weight balances are summarized in Table III as Run 8528-4.

EXAMPLE III

A 120 cm×0.9 cm column was packed with 69.9 grams of $AlPO_4$-5 (67% crystalline) slurried in toluene. An equimolar mixture of ortho-, meta-, para-xylene and ethylbenzene was then pumped through the column at a rate of 0.669 g/min. at room temperature. The inlet pressure to the column was 62 psig. After 91 grams of material had eluted, the mixed $C_8$ aromatic feed was replaced by toluene at a rate of 0.715 g/min. After a total of 208 grams of effluent was obtained, and all of the mixed $C_8$ aromatic had eluted, flows were stopped. Weight balances are summarized in Table III as Run 8528-23.

EXAMPLE IV

The packed column used in the previous runs was flushed with chlorobenzene to remove all of the toluene and to saturate the column with chlorobenzene. An equimolar mixture of ortho-, meta- and para-xylene and ethylbenzene aromatics was then pumped into the column at a rate of 0.727 g/min. at room temperature. Inlet pressure was 62 psig. After 54.5 grams of effluent were collected, the feed was switched to chlorobenzene at a rate of 0.681 g/min. After a total of 164 grams of effluent were obtained, flows were stopped. Weight balances are summarized in Table III as Run 8528-28.

TABLE III

| | Recovery of Ortho Xylene | | | |
|---|---|---|---|---|
| | 8528-1 | 8528-4 | 8528-23 | 8528-28 |
| Feed, g | | | | |
| $C_8$ Feed | 11.99 | 11.26 | 40.71 | 30.53 |
| O—Xylene Content | 3.00 | 2.82 | 10.18 | 5.11 |
| Desorbent | Toluene | Toluene | Toluene | Chlorobenzene |
| Recovery, g | | | | |
| Forecut | 1.10 | 1.10 | 4.42 | 1.60 |
| Fraction A | 0.39 | 0.92 | 2.33 | 2.33 |
| Fraction B | 0.47 | 0.58 | 2.06 | 1.67 |
| Fraction C | 0.72 | 0.52 | 0.51 | 0.55 |

TABLE III-continued

| | Recovery of Ortho Xylene | | | |
|---|---|---|---|---|
| | 8528-1 | 8528-4 | 8528-23 | 8528-28 |
| Fraction D | — | 0.09 | — | — |
| Total | 2.68 | 3.21 | 9.32 | 6.15 |
| Loss, g | 0.32 | (1.29)a | 0.86 | (1.04)a |

Note:
a = Gain

The above data in Table III indicates that as mixed $C_8$ aromatic is fed, the elutant, toluene or chlorobenzene, with which the column is saturated, is displaced. Mixed $C_8$ aromatics then elute. Initially, they contain little or no ortho-xylene but composition changes to feed composition as the adsorbent becomes saturated with orthoxylene. This fraction is labelled Forecut. The next fraction is at feed compositon and represents unnecessary feed and operating time. It is being displaced from interstitial space in the bed by the elutant. The remaining fractions represent $C_8$ aromatics that the elutant is displacing form the adsorbent. They become increasingly rich in ortho-xylene, the more strongly adsorbed component, but simultaneously the total $C_8$ content diminishes rapidly. For continuous operation, feed of $C_8$ aromatics would be resumed during this latter phase. The capacities of the sieves (for ortho-xylene) are calculated for each of these runs and are shown in Table IV below.

TABLE IV

| Capacity of $AlPO_4$-5 for ortho-Xylene Flow Runs | | |
|---|---|---|
| Run No. | $AlPO_4$-5 Crystallinity | Capacity Wt. % |
| 8528-1 | 83% | 9.4 |
| 8528-4 | 83% | 10.0 |
| 8528-23 | 68% | 7.3 |
| 8528-28 | 68% | 6.3 |

The weight % capacity of $AlPO_4$-5 for adsorbate as a function of percent crystallinity is shown for the different groups of substrates in Table IV. In general, the capacity is linear with crystallinity and is about 10-11 wt % for the pure crystalline sieve.

EXAMPLE V

A series of batch vial experiments were performed to determine that the ortho-isomer of chlorotoluene is readily separated from its meta- and para-isomers using the $AlPO_4$-5 crystalline aluminum phosphate molecular sieve.

In each batch vial experiment, one gram of $AlPO_4$-5 and ~3.5 grams of feed of known composition were sealed in a 15 ml glass centrifuge tube fitted with a 12/18 ground glass joint and matching teflon stopper. Care was taken in this procedure so that no sieve or feed was trapped in the joint allowing leakage and loss of accuracy. All weighings of feed and absorbent were finalized on a four-place analytical balance to minimize error.

The slurry was allowed to come to equilibrium overnight (16 hours) in an oscillating shaker. Each tube was then centrifuged in a Clay-Adams four-place clinical centrifuge for approximately five minutes and the supernatant liquid removed and analyzed by gas chromatography. From the differences in composition of the supernatant liquid compared to the feeds, the capacity and selectivity of the absorbent was calculated. The results are in Table V.

TABLE V

O—Chlorotoluene and Its Isomers
Separation Factors Relative to o-Xylene

| Sample No. | Toluene | 2-Chloro-toluene | 3-Chloro-toluene | 4-Chloro-toluene |
|---|---|---|---|---|
| 8528-40-1 | 0.5843 | 1.5875 | 0.4619 | −0.1424 |
| 8528-40-2 | 0.5922 | 1.5704 | 0.3163 | −0.0050 |
| 8528-40-4 | 0.4987 | 1.6332 | 0.0396 | 0.2688 |
| 8528-40-5 | 0.3972 | 1.7506 | −0.1538 | 0.1296 |
| 8528-40-6 | 0.4475 | 1.6231 | 0.2302 | 0.1286 |
| Average | 0.5040 | 1.6330 | 0.1788 | 0.0759 |

The above average separation factor of 1.6330 for 2-chlorotoluene versus the average separation factors of 0.1788 and 0.0759 for 3-chlorotoluene and 4-chlorotoluene, respectively, indicates that the ortho-isomer of chlorotoluene is readily separated from its meta- and para-isomers using the AlPO$_4$-5 crystalline aluminum phosphate molecular sieve.

EXAMPLE VI

In the procedure of Example V, 1,2-dichlorobenzene was separated from its meta- and para-isomers using AlPO$_4$-5 crystalline aluminum phosphate molecular sieve. All conditions were duplicated. Results are in Table VI.

TABLE VI

Ortho-Dichlorobenzene and Its Isomers
Separation Factors Relative to o-Xylene

| Sample No. | Toluene | 1,2-Dichloro-benzene | 1,3-Dichloro-benzene | 1,4-Dichloro-benzene |
|---|---|---|---|---|
| 8528-40-7 | 0.7490 | 1.8341 | 0.3297 | 0.3368 |
| 8528-40-9 | 0.5893 | 2.0138 | 0.2336 | 0.2748 |
| 8528-40-10 | 0.6184 | 1.8982 | 0.2537 | 0.2895 |
| 5828-40-11 | 0.5573 | 2.0439 | 0.2154 | 0.2613 |
| Average | 0.6285 | 1.9475 | 0.2581 | 0.2906 |

The above average separation factor of 1.9475 for 1,2-dichlorobenzene versus the average separation factors of 0.2581 and 0.2906 for 1,3-dichlorobenzene and 1,4-dichlorobenzene, respectfully, indicates that the ortho-isomer of dichlorobenzene is readily separated from its meta- and para-isomrrs using the AlPO$_4$-5 crystalline aluminum phosphate molecular sieve.

What is claimed is:

1. An adsorptive separation process for separating an ortho chlorinated aromatic compound selected from the group consisting of ortho-chlorotulene and ortho-dichlorobenzene from a chlorinated aromatic hydrocarbon feed stream consisting essentinlly of a mixture of meta and para isomers of said ortho chlorinated aromatic compound, which process comprises
    (a) contacting said chlorinated aromatic hydrocarbon feed stream with a bed of a crystalline alumino-phosphate adsorbent of AlPO$_4$-5;
    (b) withdrawing from said bed of adsorbent a raffinate stream containing less of the selectively adsorbed ortho chloriated aromatic compound of the feed stream;
    (c) desorbing the adsorbed ortho chlorinated aromatic compound with a desorbent to effect displacement thereof; and
    (d) withdrawing from the adsorbent bed an extract stream containing the ortho chlorinated aromatic compound.

2. The process of claim 1 wherein said feed stream comprises said ortho chlorinated aromatic compound and a mixture of aromatic hydrocarbons.

3. The process of claim 1 wherein said feed stream comprises said otho chlorinated aromatic compound and a mixture of benzene and chlorinated aromatic hydrocarbons.

4. The process of claim 1 wherein said feed stream comprises said ortho chlorinated aromatic compound and a mixture of toluene and chlorinated aromatic hydrocarbons.

5. The process of claim 1 wherein said desorbent is selected from the group consisting of toluene, benzene, chlorotoluene, dichlorobenzene, ethyltoluene, and chlorobenzene.

6. The process of claim 4 wherein said desorbent is toluene.

* * * * *

UNITED STATES PATENT OFFICE
CERTIFICATE OF CORRECTION

Patent No. 4,864,070          Dated September 5, 1989

Inventor(s) Melvern C. Hoff & Raymond C. Feld

It is certified that error appears in the above-identified patent and that said Letters Patent is hereby corrected as shown below:

| Col. | Line | | |
|------|------|---|---|
| 5  | 16 | "adepuate" should read | --adequate-- |
| 8  | 17 | "orthoxylene" should read | --ortho-xylene-- |
| 8  | 22 | "form" should read | --from-- |
| 9  | 36 | "5828" should read | --8528-- |
| 10 | 1  | "isomrrs" should read | --isomers-- |
| 10 | 8  | "essentinlly" should read | --essentially-- |
| 10 | 10 | "comprises" should read | --comprises:-- |
| 10 | 16 | "chloriated" should read | --chlorinated-- |
| 10 | 29 | "otho" should read | --ortho-- |

Signed and Sealed this

Twenty-fourth Day of July, 1990

Attest:

HARRY F. MANBECK, JR.

*Attesting Officer*    *Commissioner of Patents and Trademarks*